(12) United States Patent
Brousmiche

(10) Patent No.: US 10,822,323 B2
(45) Date of Patent: Nov. 3, 2020

(54) ACID LABILE SURFACTANTS

(71) Applicant: Waters Technologies Corporation, Milford, MA (US)

(72) Inventor: Darryl W. Brousmiche, Grafton, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 16/285,942

(22) Filed: Feb. 26, 2019

(65) Prior Publication Data

US 2019/0263774 A1    Aug. 29, 2019

Related U.S. Application Data

(60) Provisional application No. 62/635,233, filed on Feb. 26, 2018.

(51) Int. Cl.
| | | |
|---|---|---|
| *C07D 317/22* | (2006.01) | |
| *C07D 317/28* | (2006.01) | |
| *C07D 319/04* | (2006.01) | |
| *C07K 1/14* | (2006.01) | |
| *G01N 30/88* | (2006.01) | |
| *G01N 1/40* | (2006.01) | |
| *G01N 27/447* | (2006.01) | |
| *G01N 30/02* | (2006.01) | |

(52) U.S. Cl.
CPC ......... *C07D 317/22* (2013.01); *C07D 317/28* (2013.01); *C07D 319/04* (2013.01); *C07K 1/145* (2013.01); *G01N 1/4044* (2013.01); *G01N 27/44747* (2013.01); *G01N 30/02* (2013.01); *G01N 2030/8831* (2013.01)

(58) Field of Classification Search
CPC .. C07D 317/22; C07D 317/28; C07D 319/04; C07K 1/145
USPC ....................................................... 514/452
See application file for complete search history.

(56) References Cited

U.S. PATENT DOCUMENTS

2009/0292136 A1    11/2009    Powell et al.

FOREIGN PATENT DOCUMENTS

WO        2000/70334 A1    11/2000

OTHER PUBLICATIONS

International Search Report and Written Opinion for International Application No. PCT/US2019/019619, dated Jun. 7, 2019.
Ono, D., et al. "Preparation, Surface-Active Properties and Acid Decomposition Profiles of a New Soap Bearing a 1, 3-Dioxolane Ring", Journal of the American Oil Chemists ' Society (JAOCS), 70(1):29-36, Jan. 1, 1993.
Wang, G.W., e al., "Preparation, Properties, and Applications of Vesicle-Forming Cleavable Surfactants with a 1, 3-Dioxane Ring", Journal of Colloid and Interface SCI, 173(1):49-54, Jul. 1, 1995.
Hellberg, P.E., et al., "Cleavable Surfactants", Journal of Surfactants ans Detergents, 3(1): 81-91, Jan. 1, 2000.
Yu, Y.Q., et al., "Enzyme-friendly, mass spectrometry-compatible surfactant for in-solution enzymatic digestion of proteins", Analytical Chemistry, American Chemical Society, 75(21):6023-6028, Nov. 1, 2003.
International Preliminary Report on Patentability for International Application No. PCT/US2019/019619, dated Sep. 3, 2020.

*Primary Examiner* — Yevgeny Valenrod

(57) ABSTRACT

This invention relates to an acid labile surfactant. In particular, the surfactants of the present invention include a dioxolane or dioxane functional group which enables the surfactant to hydrolyze in an acidic environment. Surfactants of this type can be utilized to enhance protein solubilization/enzyme digestion. Following hydrolysis to destroy the surfactant (which may chromatographic issues), there are generally two components formed—a hydrophilic one, and a hydrophobic one. By altering the chemistry of the hydrolysable linker, the polarity of the hydrophobic residue can be altered, allowing it to be solubilized by significantly less organic solvent, and to minimize the potential loss of peptide material and to expand the chromatographic conditions that can be utilized.

29 Claims, No Drawings

ACID LABILE SURFACTANTS

CROSS REFERENCE TO RELATED APPLICATION

This application claims the benefit of U.S. Provisional Application No. 62/635,233, filed Feb. 26, 2018 and entitled "ACID LABILE SURFACTANTS", which is hereby incorporated by reference.

FIELD OF THE INVENTION

This invention relates to an acid labile surfactant. Surfactants of this type can be utilized to enhance protein solubilization/enzyme digestion. Following hydrolysis to destroy the surfactant (which may cause chromatographic issues), there are generally two components formed—a hydrophilic one, and a hydrophobic one. By altering the chemistry of the surfactant and/or hydrolysable linker, the hydrophobic residue could be made more polar, allowing it to be solubilized by significantly less organic solvent, and to minimize the potential loss of peptide material. The surfactant of the present disclosure may expand the chromatographic conditions that can be utilized; in particular, it allows for use of a larger gradient range.

BACKGROUND

Surfactants are used in a variety of applications. For example, surfactants are used commercially for cleaning manufactured items, removing paints, chemical processing, for use in emulsion polymerization, solubilizing drugs, purifying proteins, and various bioanalytical applications.

One particular bioanalytical application that uses surfactants is sodium dodecyl sulfate polyacrylamide gel electrophoresis (SDS-PAGE). In the past three decades, SDS-PAGE has been widely used as a simple and relatively rapid tool for analysis and purification of large molecules such as proteins (U.K. Laemmli, Nature 227, 680-685, 1970). Sodium dodecylsulfate (SDS) is an anionic surfactant that denatures proteins by forming a stable complex. Upon denaturation, SDS binds to most proteins and peptides in a constant weight ratio of about 1.4:1. As a result, the SDS-protein complexes have almost identical charge densities and therefore migrate in a polyacrylamide gel according to molecular weight. If the gel is of the correct porosity, a plot of log Mw vs. relative mobility, Rf, results in a linear relationship. The band intensity after staining is a rough indicator of the amount present in the sample. When coupled with another electrophoretic technique, isoelectricfocusing, SDS-PAGE can separate complex mixtures into several hundred discrete components.

The ability to estimate the size and amount of a protein has led to various applications of SDS-PAGE. However, there are some drawbacks to the technology. For example, it is very difficult to use mass spectrometry to monitor and analyze samples from DS-PAGE separations because SDS interferes with the sensitivity of mass spectrometry detection. Furthermore, it is very difficult to separate SDS from SDS/protein complex since SDS is a surfactant that forms emulsions.

Several approaches have been tried to solve these problems. Non-ionic surfactants, such as octyl β-glucopyranoside, have been used for mass spectrometric applications (P. Dainese Hatt, M. Quadroni, W. Staudenmann, and P. James, Eur. J. Biochem. 246, 336-343, 1997). However, the electrophoretic separation still requires SDS, and a time-consuming surfactant exchange step is needed.

Another approach is electroelution or electroblotting from the polyacrylamide gel onto a PVDF or nitrocellulose membrane. However, this approach often leads to significant loss in protein recovery. Other approaches that have been tried are also time-consuming and may lead to significant protein loss are: protein precipitation with guanidium chloride (J. E. Schively, in Methods of protein microcharacterization; J. E. Schively, Ed., Humana Press, Clifton, N.J., 1986, p. 41), ion-pair reagents (W. H. Koningsberg and L. H. Henderson. Methods Enzymol. 91, 254, 1983), liquid-liquid extraction (P. Davidsson, A. Westman, M. Puchades. C. L. Nilsson, and K. Blennow, Anal. Chem. 71, 642-647, 1999) and reversed-phase HPLC (H. Kawasaki and K. Suzuki, Anal. Biochem. 186, 264, 1990).

One approach to solve these problems is to use an anionic surfactant having a dioxolane or dioxane functional group which enables the surfactant to be broken down under acidic conditions. This approach has been described in U.S. patent application Ser. Nos. 11/811,696 and 10/169,002 (issued as U.S. Pat. No. 7,229,539), and these applications are incorporated herein by reference. But in the cases of material described in U.S. Pat. No. 7,229,539, after surfactant broken down under acidic conditions, the hydrophobic moiety may be too hydrophobic under certain solution conditions and precipitate out from the solution. Therefore, there is a need to modify the hydrophobicity of the hydrophobic moiety.

SUMMARY

The present invention features destructible surfactants and methods for solubilizing, analyzing, separating, purifying and/or characterizing molecules with these surfactants. In one aspect, the invention provides surfactants which may be selectively broken up at relatively low pH. The resulting breakdown products of the surfactants may be removed from the sample with relative ease or otherwise do not interfere with further chromatographic or analytical steps. The invention has applicability in a variety of techniques which benefit from the initial presence and ultimate removal of a surfactant.

Accordingly, in one aspect, the invention provides a surfactant represented by the formula (Formula I):

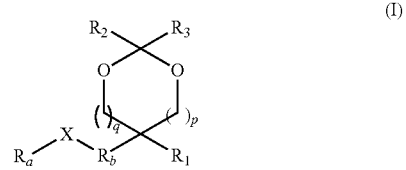

(I)

in which p and q are each, independently, 0, 1, or 2, and p+q is 1, 2, or 3;

$R_a$ and $R_b$ are each, independently, alkyl, alkenyl, or alkynyl, and $R_a$ is linear or branched $C_5$-$C_{30}$, and $R_b$ is linear or branched $C_1$-$C_5$;

X is $CR'_2$, O, NR', or S; wherein each R' is independently H, lower alkyl, lower alkenyl, or lower alkynyl;

$R_1$ and $R_2$ are each, independently, hydrogen or linear or branched $C_1$-$C_5$; and $R_3$ contains an anionic, a cationic, a zwitterionic, or a non-ionic hydrophilic group; in certain embodiments, $R_3$ is selected from —$R_4SO_3^-$, —$R_4OR_5SO_3^-$, —$R_4(OCH_2$ $CH_2)_nSO_3^-$, —$R_4COO^-$, —$R_4OR_5COO^-$, —$R_4CONCH_3CH_2COO^-$, —$R_4(OCH_2CH_2)_nOP(OH)O_2^-$, —$R_4OP(OH)O_2^-$, —$R_4OP(OH)_2O^-$, —$R_4OR_5P(OH)_2O^-$, —$R_4OR_5OP(OH)_2O^-$, —$R_4N(CH_3)_3^+$, —$R_4N(R_6)_3^+$, —$R_4OR_5N(R_6)_3^+$, —$R_4N^+(CH_3)_2CH_2COO^-$, —$R_4N(CH_3)_3^+R_5SO_3^-$; wherein $R_4$, $R_5$, and $R_6$ are each, independently, lower alkyl, lower alkenyl, lower alkynyl, substituted lower alkyl, substituted lower alkenyl, or substituted lower alkynyl; n is 1 to 6. In certain embodiments, $R_3$ can contain a phosphate, a phosphate diester, a phosphate monoester, a phosphoric acid, a phosphonate, or a phosphonic acid.

In one embodiment, $R_a$ is linear alkyl with 5-15 carbons, 7-13 carbons, or 9-11 carbons, $R_b$ is $CH_2$, and X is O.

In other aspect, surfactants of this type can be utilized to enhance protein solubilization/enzyme digestion. Following hydrolysis to destroy the surfactant, there are generally two components formed—a hydrophilic one, and a hydrophobic one. The hydrophobic component may cause chromatographic issues in subsequent steps following the solubilization/enzyme digestion; for example, the hydrophobic component may precipitate out from high aqueous solutions—taking peptides with it and/or selectively taking more non-polar peptides—and alter peptide recoveries and/or peptide ratios. By altering the chemistry of the surfactant and/or hydrolysable linker, the hydrophobic residue could be made more polar, allowing it to be solubilized by significantly less organic solvent, and to minimize the potential loss of peptide material, and to expand the chromatographic conditions that can be utilized.

In one embodiment, the invention pertains to methods for analyzing a sample which include contacting the sample with a surfactant having the structure of Formula I. In another embodiment, the method includes analyzing the sample by high performance liquid chromatography (HPLC). In still another embodiment, the method includes analyzing the sample by mass spectrometry (MS) or LC-MS. In yet another embodiment, the method includes analyzing the sample by ion-pair liquid chromatography.

In another embodiment, the invention provides a method for performing electrophoresis which includes contacting a sample with a surfactant having the structure of Formula I. In another embodiment, the electrophoresis is gel electrophoresis or, particularly, polyacrylamide gel electrophoresis, including the tube, slab gel and capillary formats of polyacrylamide gel electrophoresis. In other embodiments, the electrophoresis is free zone electrophoresis or capillary electrophoresis. In still other embodiments, the methods include the step of degrading the surfactant after electrophoresis. In another embodiment, the method includes degrading the surfactant after electrophoresis with a relatively acidic solution. In yet another embodiment, the method includes the step of further purifying the sample after degrading the surfactant.

In another embodiment, the invention provides a method for performing enzymatic digestion of protein without including any prior purification steps with a surfactant having the structure of Formula I. In another embodiment, the methods include the step of degrading the surfactant after enzymatic digestion of protein. In another embodiment, the method includes degrading the surfactant after enzymatic digestion of protein with a relatively acidic solution. In yet another embodiment, the method includes the step of further purifying the peptides after degrading the surfactant.

In still another embodiment, the invention provides a kit for performing electrophoresis which includes a surfactant having the structure of Formula I. In another embodiment, the kit includes a component for degrading the surfactant. In another embodiment, the kit includes a molecular weight standard. In yet another embodiment, the kit includes a staining reagent. In another embodiment, the surfactant of the invention is incorporated into a gel medium.

DETAILED DESCRIPTION

Overview of the Invention

This invention pertains to surfactants, including the synthesis and use of surfactants. In particular, the surfactants of the present invention include a dioxolane or dioxane functional group which enables the surfactant to break down in an acidic environment. The resulting degradant products can be removed from the matrix more readily than the original surfactant, and/or minimize chromatographic issues in subsequent steps following the protein solubilization/enzyme digestion step.

In one aspect, this invention pertains to anionic surfactants, including the synthesis and use of anionic surfactants. In particular, the invention includes anionic surfactants with protein-binding and electrophoretic properties similar to SDS. Unlike SDS, however, the surfactants of the present invention include a dioxolane or dioxane functional group which enables the surfactant to break down in an acidic environment. The resulting degradant products can be removed from the matrix more readily than the original surfactant or otherwise do not interfere with further chromatographic or analytical steps. In addition, mass spectrometric sensitivity of proteins may be significantly and surprisingly greater than in the presence of SDS at similar concentrations, even in the presence of these degradant products.

The destructible surfactants may be prepared as shown in the examples described in this application and in U.S. Pat. No. 7,229,539. These surfactants have functionality similar to SDS but, unlike SDS, they may be hydrolyzed in aqueous acid solution under mild condition to give two nonsurfactant products: an ionic, water-soluble compound and a neutral, less water soluble compound. The surfactants of the present invention may be used in applications which benefit from the initial presence and ultimate removal of a surfactant. In particular, the present invention is useful for the solubilization, analysis, separation, purification and/or characterization of large molecules.

In addition, following hydrolysis to destroy the surfactant, there are generally two components formed—a hydrophilic one, and a hydrophobic one. The hydrophobic component may cause chromatographic issues in subsequent steps following the solubilization/enzyme digestion; for example, the hydrophobic component may precipitate out from the solution—taking peptides with it and/or selectively taking more non-polar peptides—and alter peptide recoveries and/or peptide ratios. By altering the chemistry and/or hydrolysable linker of the surfactant disclosed in U.S. Pat. No. 7,229,539, the hydrophobic residue could be made more polar, allowing it to be solubilized by significantly less organic solvent, and to minimize the potential loss of peptide material, and to expand the chromatographic conditions that can be utilized.

So that the invention may be more readily understood, a number of terms are first defined.

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 20 or fewer carbon atoms in its backbone (e.g., $C_1$-$C_{20}$ for straight chain, $C_3$-$C_{20}$ for branched chain).

Unless the number of carbon atoms is otherwise specified, the term "lower alkyl" refers to an alkyl group having from one to ten carbons. In certain embodiments, a lower alkyl group has 2 to 6 carbon atoms, or, particularly, 3 or 4 carbon atoms.

The term "alkenyl" refers to an unsaturated hydrocarbon group that includes a set of carbon-carbon double bonds, including straight-chain alkenyl groups, branched-chain alkenyl groups, cycloalkenyl (alicyclic) groups, alkyl substituted cycloalkenyl groups, and cycloalkyl substituted alkenyl groups. In some embodiments, a straight chain or branched chain alkenyl has 20 or fewer carbon atoms in its backbone (e.g., $C_2$-$C_{20}$ for straight chain, $C_4$-$C_{20}$ for branched chain).

Unless the number of carbon atoms is otherwise specified, the term "lower alkenyl" refers to an alkenyl group having from two to ten carbons. In certain embodiments, a lower alkenyl group has 2 to 6 carbon atoms or, particularly, 3 or 4 carbon atoms.

The term "alkynyl" refers to an unsaturated hydrocarbon group that includes a set of carbon-carbon triple bonds, including straight-chain alkynyl groups, branched-chain alkynyl groups, cycloalkynyl groups, alkyl substituted cycloalkynyl groups, and cycloalkyl substituted alkynyl groups. In certain embodiments, a straight chain or branched chain alkynyl has 20 or fewer carbon atoms in its backbone (e.g., $C_2$-$C_{20}$ for straight chain, $C_4$-$C_{20}$ for branched chain).

Unless the number of carbon atoms is otherwise specified, the term "lower alkynyl" refers to an alkynyl group having from two to ten carbons. In some embodiments, a lower alkenyl group has 2 to 6 carbon atoms or, particularly, 3 or 4 carbon atoms.

The term "sample/surfactant complex" refers to the complex formed by a surfactant of the present invention and a sample.

The term "sample" refers to any molecule that may be used in the present invention. Examples include, without limitation, macromolecules. Particular examples include proteins or peptides.

The term "lipophilic protein" refers to proteins or peptides that are relatively hydrophobic. Examples include, without limitation, protein from myelin or central nervous system tissue and membrane-bound proteins such as receptors.

The term "receptor" is recognized in the art and refers generally to membrane-bound molecules, including, but not limited to, proteins, which bind a ligand and transmit a signal into the cell. Such receptors usually have an extracellular domain, a transmembrane domain, and an intracellular domain.

The term "inclusion body" is recognized in the art and refers to an intracellular structure, including, but not limited to, one containing an expressed protein.

The term "solution for degrading the surfactant" refers broadly to any relatively low pH solution. In certain embodiments, the pH of the solution is between 0 and 5. In still other embodiments, the pH of the solution is between 1 and 3. In general, the lower the pH of the solution for degrading the surfactant, the less time required to degrade the surfactant. In addition, the compound used to make the solution for degrading the surfactant is not particularly limited: any compound that provides a relatively low pH solution suitable for degrading the surfactants of the present invention without damaging the sample is sufficient. Thus, for example, hydrochloric acid may be used as the solution for degrading the surfactant. In particular embodiments, trifluoroacetic-acid (TFA) may be used. In other embodiments, acetic or formic acid may be used as the solution for degrading the surfactant.

The term "electrophoresis" refers to any of the various methods of analyzing molecules by their rate of movement in an electric field, i.e. based on the charge to mass ratio of the molecules. Examples include, but are not limited to, gel electrophoresis, polyacrylamide gel electrophoresis, including the tube, slab gel and capillary formats of polyacrylamide gel electrophoresis, free zone electrophoresis and capillary electrophoresis.

The term "analysis" or "analyzing" refers to any of the various methods of separating, purifying, solubilizing, and/or characterizing large molecules, such as proteins or peptides. Examples include, but are not limited to, electrophoresis, mass spectrometry, high performance liquid chromatography, ion-pair liquid chromatography, liquid-liquid extraction and ultraviolet detection.

The term "mass spectrometric detection" refers to any of the various methods of as spectroscopy. Examples include, but are not limited to, electrospray ionization ("ESI") and Matrix Assisted Laser Desorption Ionization ("MALDI").

Compounds of the Invention

In one aspect, the invention provides a surfactant represented by the formula (Formula I):

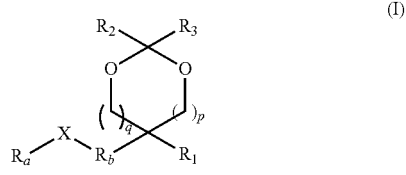

in which p and q are each, independently, 0, 1, or 2, and p+q is 1, 2, or 3;

$R_a$ and $R_b$ are each, independently, alkyl, alkenyl, or alkynyl, and $R_a$ is linear or branched $C_5$-$C_{30}$, and $R_b$ is linear or branched $C_1$-$C_5$;

X is $CR'_2$, O, NR', or S; wherein each R' is independently H, lower alkyl, lower alkenyl, or lower alkynyl;

$R_1$ and $R_2$ are each, independently, hydrogen or linear or branched $C_1$-$C_5$; and $R_3$ contains an anionic, a cationic, a zwitterionic, or a non-ionic hydrophilic group; in certain embodiments, $R_3$ is selected from —$R_4SO_3^-$, —$R_4OR_5SO_3^-$, —$R_4(OCH_2CH_2)_nSO_3^-$, —$R_4COO^-$, —$R_4OR_5COO^-$, —$R_4CONCH_3CH_2COO^-$, —$R_4(OCH_2CH_2)_nOP(OH)O_2^-$, —$R_4OP(OH)O_2^-$, —$R_4OP(OH)_2O^-$, —$R_4OR_5P(OH)_2O^-$, —$R_4OR_5OP(OH)_2O^-$, —$R_4N(CH_3)_3^+$, —$R_4N(R_6)_3^+$, —$R_4OR_5N(R_6)_3^+$, —$R_4N^+(CH_3)_2CH_2COO^-$, —$R_4N(CH_3)_3^+R_5SO_3^-$; wherein $R_4$, $R_5$, and $R_6$ are each, independently, lower alkyl, lower alkenyl, lower alkynyl, substituted lower alkyl, substituted lower alkenyl, or substituted lower alkynyl; n is 1 to 6. In certain embodiments, the substituents in the substituted lower alkyl, substituted lower alkenyl can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. In particular embodiments, the substituents in the substituted lower alkyl, substituted lower alkenyl are fluorine substituents.

In some embodiments, q is 1, and p is 0 or 1. In some other embodiments, $R_a$ is an alkyl having from six to twenty carbon atoms, more specifically from eight to eighteen carbon atoms or from ten to sixteen carbon atoms. In certain embodiments, $R_b$ is an alkyl having one to three carbon atoms, more specifically is a $CH_2$ group. In certain embodiment, X is O. In certain embodiments, $R_3$ is —$R_4SO_3^-$, —$R_4OR_5SO_3^-$, or —$R_4(OCH_2CH_2)_nSO_3^-$; particularly, $R_3$ is —$CH_2O(CH_2)_3SO_3^-$ or —$CH_2O(CH_2)_4SO_3^-$. In certain embodiments, $R_4$ and $R_5$ are each, independently, an alkyl, alkenyl, or alkynyl group having from one to eight carbons, more specifically from two to six carbon atoms, and more specifically, three or four carbon atoms.

In certain embodiment, $R_a$ is linear alkyl with 5-15 carbons, 7-13 carbons, or 9-11 carbons, $R_b$ is $CH_2$, and X is O.

In another embodiment, the surfactants of the invention have the structure of general formula (Formula II):

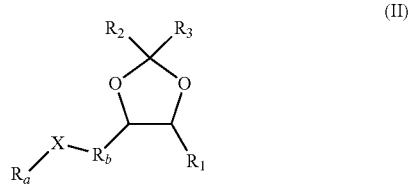

in which
$R_a$ and $R_b$ are each, independently, alkyl, alkenyl, or alkynyl, and $R_a$ is linear or branched $C_5$-$C_{30}$, and $R_b$ is linear or branched $C_1$-$C_5$;
X is $CR'_2$, O, NR', or S; wherein each R' is independently H, lower alkyl, lower alkenyl, or lower alkynyl;
$R_1$ and $R_2$ are each, independently, hydrogen or linear or branched $C_1$-$C_5$; and
$R_3$ contains an anionic, a cationic, a zwitterionic, or a non-ionic hydrophilic group; in certain embodiments, $R_3$ is selected from —$R_4SO_3^-$, —$R_4OR_5SO_3^-$, —$R_4(OCH_2CH_2)_nSO_3^-$, —$R_4COO^-$, —$R_4OR_5COO^-$, —$R_4CONCH_3CH_2COO^-$, —$R_4(OCH_2CH_2)_nOP(OH)O_2^-$, —$R_4OP(OH)O_2^-$, —$R_4OP(OH)_2O^-$, —$R_4OR_5P(OH)_2O^-$, —$R_4OR_5OP(OH)_2O^-$, —$R_4N(CH_3)_3^+$, —$R_4N(R_6)_3^+$, —$R_4OR_5N(R_6)_3^+$, —$R_4N^+(CH_3)_2CH_2COO^-$, —$R_4N(CH_3)_3^+R_5SO_3^-$; wherein $R_4$, $R_5$, and $R_6$ are each, independently, lower alkyl, lower alkenyl, lower alkynyl, substituted lower alkyl, substituted lower alkenyl, or substituted lower alkynyl; n is 1 to 6. In certain embodiments, the substituents in the substituted lower alkyl, substituted lower alkenyl can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. In particular embodiments, the substituents in the substituted lower alkyl, substituted lower alkenyl are fluorine substituents.

In one embodiment, $R_a$ is linear alkyl with 5-15 carbons, 7-13 carbons, or 9-11 carbons, $R_b$ is $CH_2$, and X is O.

In other embodiments, $R_a$ is an alkyl having from six to twenty carbon atoms, more specifically from eight to eighteen carbon atoms or from ten to sixteen carbon atoms. In certain embodiments, $R_b$ is an alkyl having one to three carbon atoms, more specifically is a $CH_2$ group. In certain embodiment, X is O. In certain embodiments, $R_3$ contains an anionic surfactant group selected from —$R_4SO_3^-$, —$R_4OR_5SO_3^-$, or —$R_4(OCH_2CH_2)_nSO_3^-$. In particular embodiments, $R_3$ is —$CH_2O(CH_2)_3SO_3^-$ or —$CH_2O$ $(CH_2)_4SO_3^-$. In certain embodiments, $R_4$ and $R_5$ are each, independently, an alkyl group having from one to eight carbons, more specifically from two to six carbon atoms, and more specifically, three or four carbon atoms.

In certain embodiments, the surfactant of the invention has the following chemical structure:

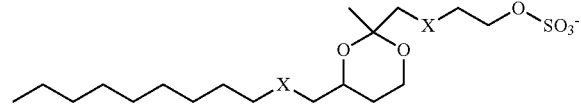

wherein X is independently O, NR', NH, S, or $CH_2$; R' is H, lower alkyl, lower alkenyl, or lower alkynyl.

In some embodiments, the surfactant of the invention has the following chemical structures.

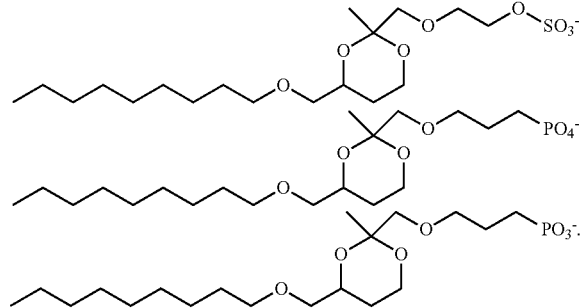

In certain embodiments, the surfactant of the invention has the following chemical structure:

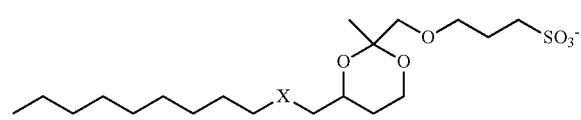

wherein X is independently O, NR', NH, S, or $CH_2$; R' is H, lower alkyl, lower alkenyl, or lower alkynyl.

In some embodiments, the surfactant of the invention has the following chemical structures.

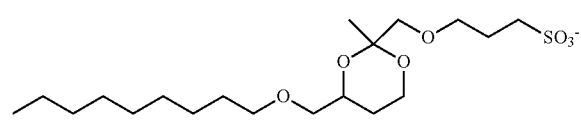

-continued

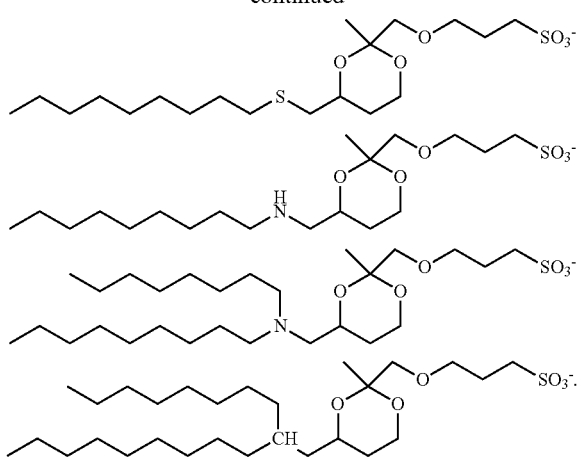

In certain embodiments, the surfactant of the invention has the following chemical structure:

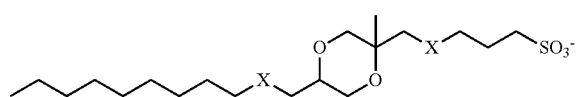

wherein X is independently O, NR', NH, S, or CH$_2$; R' is H, lower alkyl, lower alkenyl, or lower alkynyl.

In some embodiments, the surfactant of the invention has the following chemical structures.

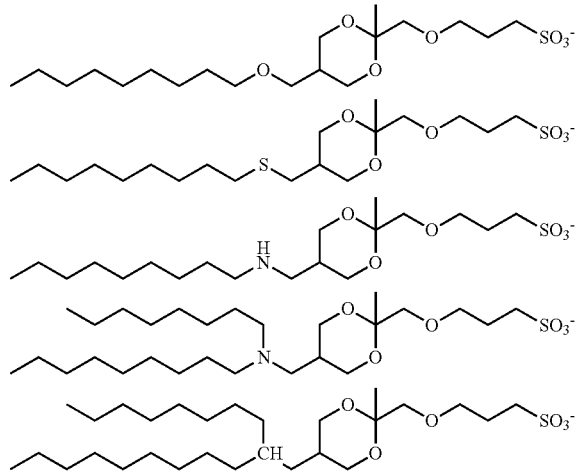

In one embodiment, the surfactant of the invention has the following chemical structure.

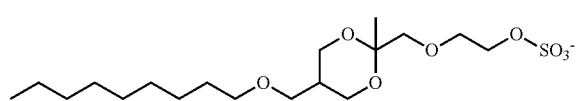

In certain embodiments, the surfactant of the invention has the following chemical structure:

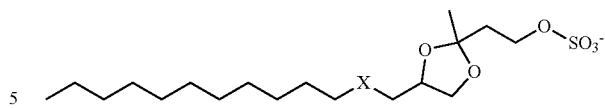

wherein X is O, NR', NH, S, or CH$_2$; R' is H, lower alkyl, lower alkenyl, or lower alkynyl.

In some embodiments, the surfactant of the invention has the following chemical structures.

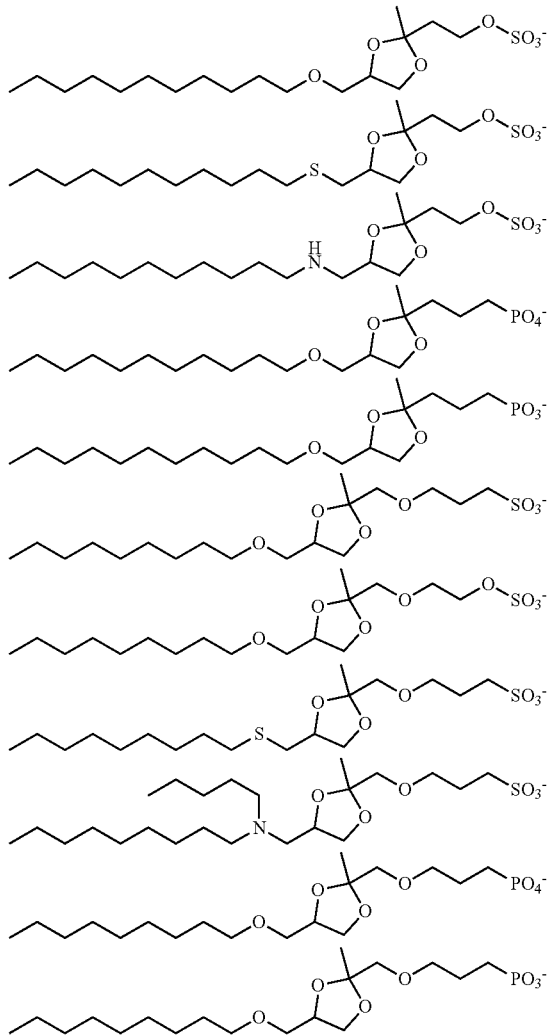

As indicated in more detail in the Examples, the methods of synthesis of the present invention produce isomers. Although the methods of using surfactants of the invention do not require separation of these isomers, such separation may be accomplished, if desired, by methods known in the art. For example, preparative high performance liquid chromatography methods may be used for isomer purification.

Methods of the Invention

The surfactants of the present invention may be used in applications that benefit from the initial presence and ultimate removal of a surfactant. In particular, the present invention is useful for the solubilization, analysis, separation, isolation, purification, detection and/or characterization of molecules from biological samples, such as biological fluids, biological tissues, biological matrices, embedded tissue samples, and cell culture supernatants.

In one embodiment, the invention provides methods for analysis of a molecule, which includes contacting the sample containing at least one molecule with a surfactant of the present invention, to thereby analyze the molecule. In certain embodiments, the sample may be heated either before or after contacting the sample with a surfactant of the invention. In certain embodiments, the step of analyzing the sample includes electrophoresis. In particular embodiments, the electrophoresis is free zone electrophoresis or capillary electrophoresis.

Analysis of the sample may include, without limitation, solid phase extraction, solid phase micro extraction, electrophoresis, mass spectrometry, e.g., MALDI-MS or ESI, liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

Another embodiment of the invention provides a method for performing cell lysis comprising contacting a cell containing at least one molecule with a surfactant of the present invention, to thereby lyse the cell. In certain embodiments, analysis, e.g., mass spectroscopy or electrophoresis, is performed on the molecule after cell lysis. In certain embodiments, the surfactant is degraded after electrophoresis. Degradation of the surfactant can be performed by contacting the surfactant with an acidic solution. In specific embodiments, the molecule is purified, e.g., by solid phase extraction or HPLC after degradation of the surfactant.

In another embodiment, the invention provides a kit for performing cell lysis on a sample containing at least one molecule to isolate the molecule comprising a surfactant of the present invention, and instructions for use. In certain embodiments, the kit can additionally include a solution for degrading the surfactant or a solid phase extraction device.

An additional embodiment of this invention uses destructible surfactants of the invention to complex with mixtures, e.g., biological samples, e.g., cell cultures, containing at least one molecule for electrophoresis. After the electrophoretic separation, the separated components, e.g., small molecules and proteins, are released from the surfactants of the present invention by treating with acid solution. The isolated molecules may be further purified by conventional separation methods such as liquid-liquid extraction, solid-phase extraction or liquid chromatography. This ability to release the molecules from surfactants easily after electrophoresis may be used in various applications, with significant benefits to separation science.

In other embodiments, the step of analyzing the sample after protein solubilization/enzyme digestion includes electrophoresis. In certain embodiments, the electrophoresis is gel electrophoresis, free zone electrophoresis or capillary electrophoresis. In a particular embodiment, the electrophoresis is polyacrylamide gel electrophoresis, including the tube, slab gel and capillary formats of polyacrylamide gel electrophoresis.

In still other embodiments, the step of analyzing the sample includes mass spectrometric determination, high performance liquid chromatography, ion-pair liquid chromatography, liquid-liquid extraction, or ultraviolet detection.

In one aspect, this invention uses destructible surfactants to complex with protein mixtures for polyacrylamide gel electrophoresis. After the electrophoretic separation, the proteins are freed from surfactants by treating the gel with acid solution. The protein mixtures may be further purified by conventional separation methods such as liquid-liquid extraction, solid-phase extraction or liquid chromatography. This ability to free proteins from surfactants easily after polyacrylamide gel electrophoresis may be used in various applications, with significant benefits to separation science.

As demonstrated by the PAGE results herein, proteins treated with the acid-labile surfactants of the present invention migrate in a similar pattern to proteins treated with SDS. In addition, the gel staining procedures are similar in the presence of either ALS or SDS.

The invention also provides methods for solubilizing various substances, such as inclusion bodies, lipophilic proteins, such as receptors and other membrane-bound proteins, and biological tissue. In a particular embodiments, the invention provides a method for obtaining a protein expressed in a cell by treating the inclusion bodies of the cell with a surfactant having the structure of Formula I.

In yet another embodiment, the invention provides a method for cleaning and/or regenerating HPLC columns. In another embodiment, a surfactant having the structure of Formula I is contacted with the sorbent of an HPLC column such that proteins bound to the column are removed.

EXEMPLIFICATION

The invention is further illustrated by the following examples that should not be construed as limiting.

This invention utilizes changes in the chemical bonding order of the reagent such that upon hydrolysis the hydrophobic group is significantly more soluble in the standard buffer solution than the equivalent group from the surfactant disclosed in U.S. Pat. No. 7,229,539, identified as Compound 1 below. The chemical properties of the hydrophobic groups can also be altered to enhance this solubility. This includes the use of embedded polar groups and side chains.

Two exemplary surfactants 4 and 7, which differ in the alkyl chain length, are generated for investigation. Both have the same hydrophilic hydrolysis product 5. The major difference from Compound 1 is that upon hydrolysis of the cyclic acetal, the diol functionality will be on the alkyl chain rather than the polar molecule. In addition, the alkyl chain will now have an optional embedded ether functionality in compare to surfactant 1 as previous reported.

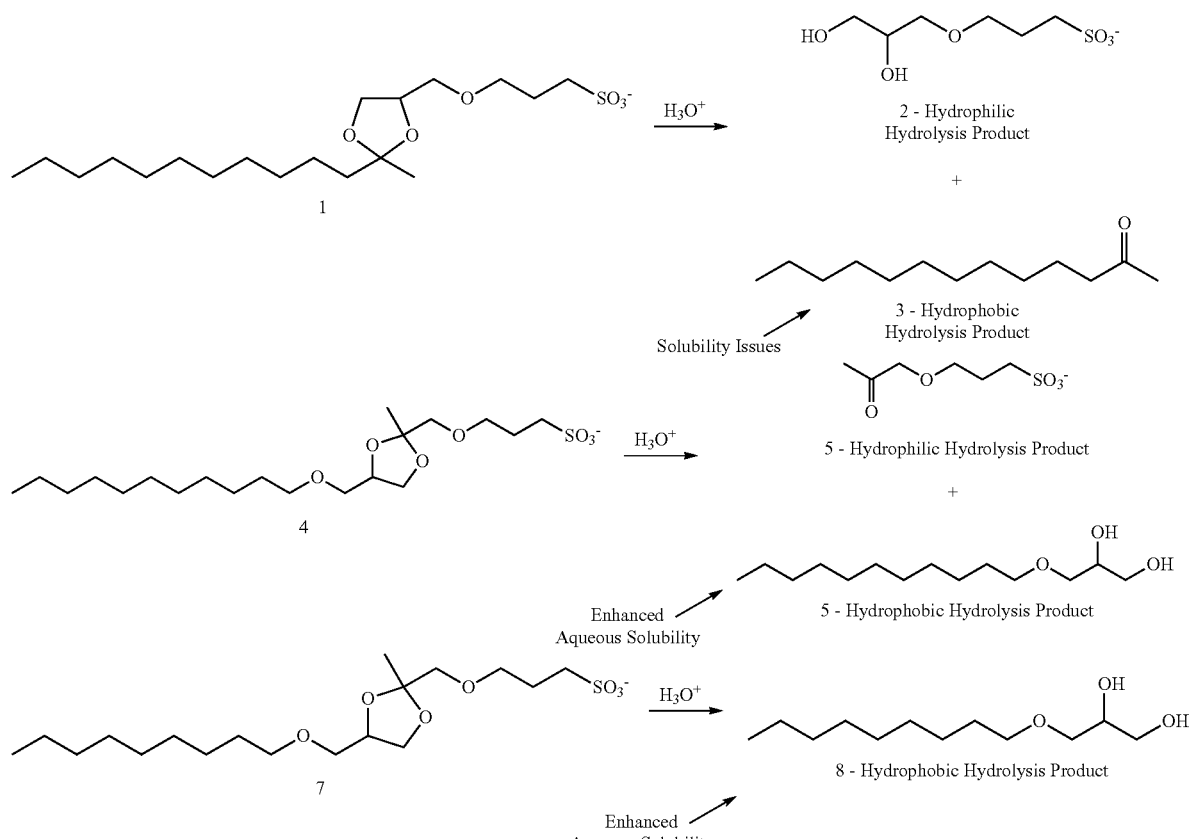

The hydrophilic hydrolysis products from these reagents have log P coefficients that are calculated to be approximately 0.9-1.4 orders of magnitude smaller than compound 3, indicating that they should be more soluble in water than the latter, the hydrophobic component of Compound 1.

TABLE 1

Calculated logP of selected hydrolysis products of surfactant compounds 1, 4, and 7

| Compound | Calculated logP (SciFinder) |
| --- | --- |
| 1 | / |
| 2 | −2.90 (non-ionized) |
| 3 | 5.05 |
| 4 | / |
| 5 | / |
| 6 | 4.15 |
| 7 | / |
| 8 | 3.65 |

Example 1

Preparation of Selected Hydrophobic Moieties

This example describes the preparation of certain hydrophobic moieties of the present invention. Various modifications to the following procedures will be routine to one of ordinary skill in the art, in light of the teachings herein.

1. Synthesis of 3-(undecyloxy)-1,2-propanediol (Compound 6)

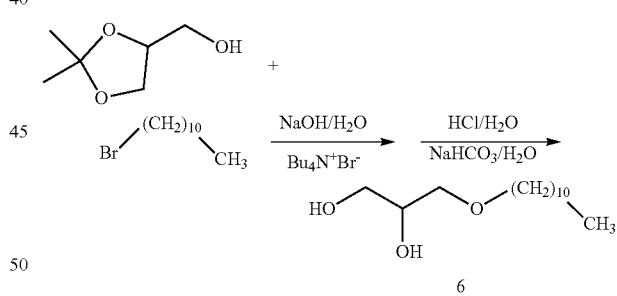

3.3 g of DL-1,2-O-isopropylidene glycerol was added to a solution of freshly prepared 50% aq. NaOH (50 mL). Stirring was started, and the mixture was heated to 80° C. and held at temperature for 1 hour. After this time, 1-bromoundecane (15.8 g) and t-butylammonium bromide (1.3 g) were successively added and heating was maintained for 7 hours.

After cooling to room temperature, the mixture was poured into water (150 mL) and extracted with $CH_2Cl_2$ (50 mL×3). The combined organic extracts were washed with water (25 mL×2), dried ($Na_2SO_4$) and concentrated to provide the crude product. This crude was dissolved in a mixture of ethanol (20 mL) and 2 M aq. HCl (30 mL) and refluxed for 1 h. The ethanol was removed using a rotary evaporator, and the remaining aqueous phase was neutralized with a saturated NaHCO$_3$ solution and extracted with CH$_2$Cl$_2$. The organic extract was dried and concentrated before purification by column chromatography (3:1 ethylacetate:petroleum ether) to afford pure 3-(undecyloxy)-1,2-propanediol (Compound 6) (4.6 g, 75% yield).

2. Synthesis of 3-nonoxypropane-1,2-diol (Compound 8)

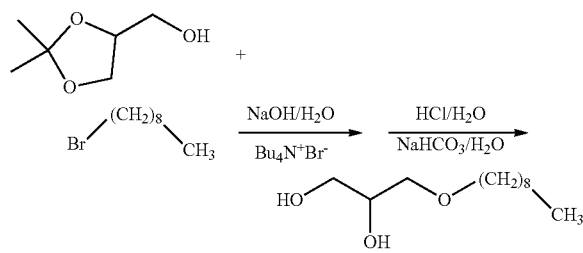

3.3 g of DL-1,2-O-isopropylidene glycerol was added to a solution of freshly prepared 50% aq. NaOH (50 mL). Stirring was started, and the mixture was heated to 80° C. and held at temperature for 1 hour. After this time, 1-bromononane (13.9 g) and t-butylammonium bromide (1.3 g) were successively added and heating was maintained for 7 hours.

After cooling to room temperature, the mixture was poured into water (150 mL) and extracted with CH$_2$Cl$_2$ (50 mL×3). The combined organic extracts were washed with water (25 mL×2), dried (Na$_2$SO$_4$) and concentrated to provide the crude product. This crude was dissolved in a mixture of ethanol (20 mL) and 2 M aq. HCl (30 mL) and refluxed for 1 h. The ethanol was removed using a rotary evaporator, and the remaining aqueous phase was neutralized with a saturated NaHCO$_3$ solution and extracted with CH$_2$Cl$_2$. The organic extract was dried and concentrated before purification by column chromatography (3:1 ethylacetate:petroleum ether) to afford pure 3-(nonyloxy)-1,2-propanediol (Compound 8) (4.1 g, 67% yield).

Example 2

Dissolution Study of Selected Hydrophobic Moieties

A dissolution study was performed on compounds 3 (commercially available—Sigma Aldrich P/N 172839 99%) 6, and 8 (Synthesis described above) at 21° C. in different buffer solutions containing a mixture of standard chromatographic solvents, e.g., acetonitrile and 20 mM aqueous ammonium carbonate. 20 mM aqueous ammonium bicarbonate was made by dissolving 474 mg ammonium bicarbonate in 300 mL MiliQ water. The results are presented in Tables 2 and 3.

TABLE 2

Solubility of selected hydrophobic moieties in a buffer solution of 30 mL acetonitrile and 70 mL 20 mM ammonium bicarbonate (30% acetonitrile)

| Compound | Weight (mg) | Buffer solution (mL) | Observed Solubility | Solubility (mg/mL) |
|---|---|---|---|---|
| 3 | 30 | 50 | At 30 mg: Not dissolved in buffer solution | <1 |
| 6 | 80 ± 10 | 10 | At 70 mg: Dissolved in buffer solution At 90 mg: Not dissolved in buffer solution | ~8 ± 1 |
| 8 | 200 | 1.4 | At 200 mg: Dissolved in buffer solution | ~140 |

TABLE 3

Solubility of selected hydrophobic moieties in a buffer solution of 10 mL acetonitrile and 90 mL 20 mM ammonium bicarbonate (10% acetonitrile)

| Compound | Weight (mg) | Buffer solution (mL) | Observed Solubility | Solubility (mg/mL) |
|---|---|---|---|---|
| 3 | 6 | 180 mL | At 6 mg: Not dissolved in buffer solution | <0.03 |
| 6 | 6 | 120 mL | At 6 mg: Not dissolved in buffer solution | <0.05 |
| 8 | 12 | 24 mL | At 12 mg: Dissolved in buffer solution | ~0.5 |

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

The invention claimed is:

1. A method for performing protein solubilization or enzyme digestion comprising contacting a sample with a surfactant represented by the Formula I:

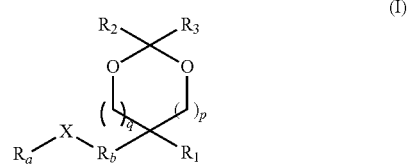

in which
p and q are each, independently, 0, 1, or 2, and p+q is 1, 2, or 3;
R$_a$ and R$_b$ are each, independently, alkyl, alkenyl, or alkynyl, and R$_a$ is linear or branched C$_5$-C$_{30}$, and R$_b$ is linear or branched C$_1$-C$_5$;

X is CR'$_2$, O, NR', or S; wherein each R' is independently H, lower alkyl, lower alkenyl, or lower alkynyl;

R$_1$ and R$_2$ are each, independently, hydrogen or linear or branched C$_1$-C$_5$; and R$_3$ is a group selected from —R$_4$SO$_3^-$, —R$_4$OR$_5$SO$_3^-$, —R$_4$(OCH$_2$CH$_2$)$_n$SO$_3^-$, —R$_4$OR$_5$COO$^-$, —R$_4$CONCH$_3$CH$_2$COO$^-$, —R$_4$(OCH$_2$CH$_2$)$_n$OP(OH)O$_2^-$, —R$_4$OP(OH)O$_2^-$, —R$_4$OP(OH)$_2$O$^-$, —R$_4$OR$_5$P(OH)$_2$O$^-$, —R$_4$OR$_5$OP(OH)$_2$O$^-$, —R$_4$OR$_5$N(R$_6$)$_3^+$, —R$_4$N$^+$(CH$_3$)$_2$CH$_2$COO$^-$, or —R$_4$N(CH$_3$)$_3^+$R$_5$SO$_3^-$; wherein R$_4$, R$_5$, and R$_6$ are each, independently, lower alkyl, lower alkenyl, lower alkynyl, substituted lower alkyl, substituted lower alkenyl, or substituted lower alkynyl; n is 1 to 6.

2. The method of claim 1, wherein R$_3$ is selected from a group consisting of —R$_4$SO$_3^-$, —R$_4$OR$_5$SO$_3^-$, —R$_4$(OCH$_2$CH$_2$)$_n$SO$_3^-$.

3. The method of claim 1 comprising the further step of degrading the surfactant after protein solubilization or enzyme digestion.

4. The method of claim 3 wherein the step of degrading the surfactant after protein solubilization or enzyme digestion comprises contacting the surfactant with an acidic solution.

5. The method of claim 3 comprising the further step of purifying the sample.

6. A method for performing protein solubilization or enzyme digestion comprising contacting a sample with a surfactant that is represented by the following formula:

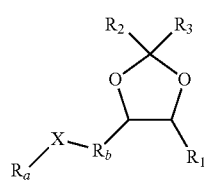

(II)

in which

R$_a$ and R$_b$ are each, independently, alkyl, alkenyl, or alkynyl, and R$_a$ is linear or branched C$_5$-C$_{30}$, and R$_b$ is linear or branched C$_1$-C$_5$;

X is CR'$_2$, O, NR', or S; wherein each R' is independently H, lower alkyl, lower alkenyl, or lower alkynyl;

R$_1$ and R$_2$ are each, independently, hydrogen or linear or branched C$_1$-C$_5$; and R$_3$ contains an anionic, a cationic, a zwitterionic, or a non-ionic hydrophilic group;

to form a sample/surfactant complex.

7. The method of claim 6, wherein R$_3$ is selected from a group consisting of —R$_4$SO$_3^-$, —R$_4$OR$_5$SO$_3^-$, —R$_4$(OCH$_2$CH$_2$)$_n$SO$_3^-$, —R$_4$COO$^-$, —R$_4$OR$_5$COO$^-$, —R$_4$CONCH$_3$CH$_2$COO$^-$, —R$_4$(OCH$_2$CH$_2$)$_n$OP(OH)O$_2^-$, —R$_4$OP(OH)O$_2^-$, —R$_4$OP(OH)$_2$O$^-$, —R$_4$OR$_5$P(OH)$_2$O$^-$, —R$_4$OR$_5$OP(OH)$_2$O$^-$, —R$_4$N(CH$_3$)$_3^+$, —R$_4$N(R$_6$)$_3^+$, —R$_4$OR$_5$N(R$_6$)$_3^+$, —R$_4$N$^+$(CH$_3$)$_2$CH$_2$COO$^-$, —R$_4$N(CH$_3$)$_3^+$R$_5$SO$_3^-$; wherein R$_4$, R$_5$, and R$_6$ are each, independently, lower alkyl, lower alkenyl, lower alkynyl, substituted lower alkyl, substituted lower alkenyl, or substituted lower alkynyl; n is 1 to 6.

8. The method of claim 6, wherein R$_3$ is selected from a group consisting of —R$_4$SO$_3^-$, —R$_4$OR$_5$SO$_3^-$, —R$_4$(OCH$_2$CH$_2$)$_n$SO$_3^-$.

9. The method of claim 1 wherein the surfactant is selected from the following chemical structures:

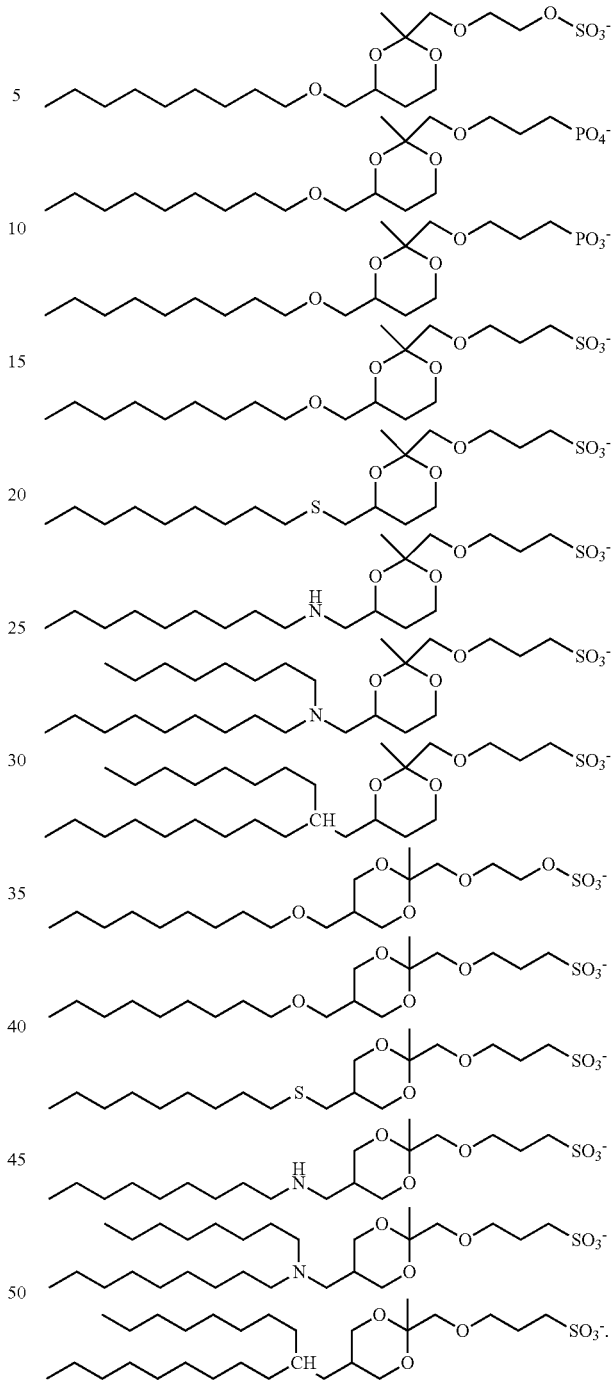

10. The method of claim 1 wherein the surfactant is selected from the following chemical structures:

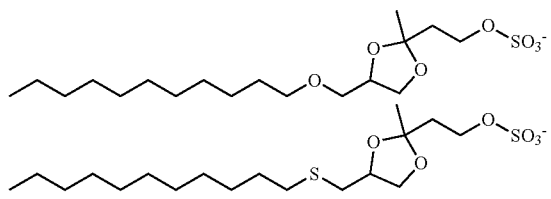

-continued

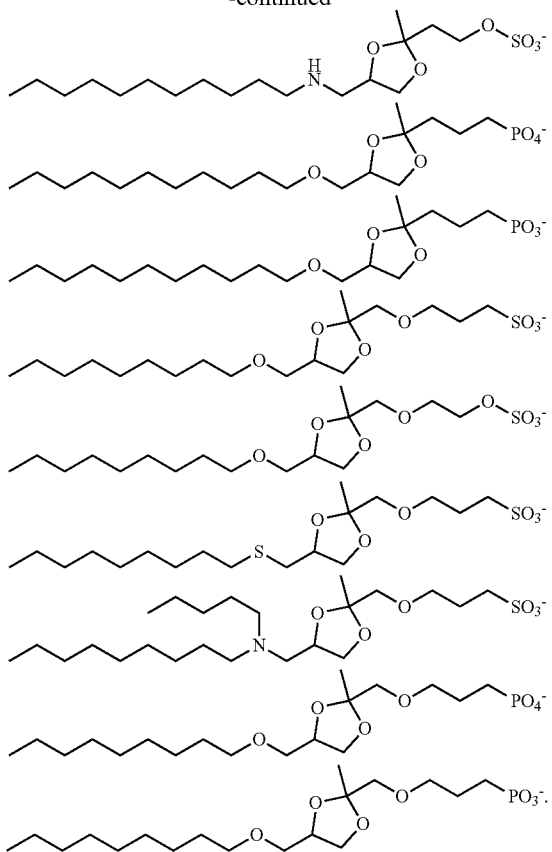

11. A surfactant having the following chemical structure:

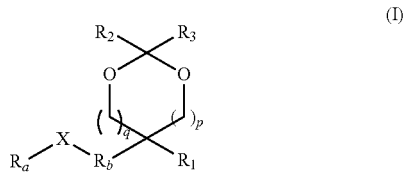

(I)

in which p and q are each, independently, 0, 1, or 2, and p+q is 1, 2, or 3;

$R_a$ and $R_b$ are each, independently, alkyl, alkenyl, or alkynyl, and $R_a$ is linear or branched $C_5$-$C_{30}$, and $R_b$ is linear or branched $C_1$-$C_5$;

X is $CR'_2$, O, NR', or S; wherein each R' is independently H, lower alkyl, lower alkenyl, or lower alkynyl;

$R_1$ and $R_2$ are each, independently, hydrogen or linear or branched $C_1$-$C_5$; and $R_3$ is a group selected from —$R_4SO_3^-$, —$R_4OR_5SO_3^-$, —$R_4(OCH_2CH_2)_nSO_3^-$, —$R_4OR_5COO^-$, —$R_4CONCH_3CH_2COO^-$, —$R_4(OCH_2CH_2)_nOP(OH)O_2^-$, —$R_4OP(OH)O_2^-$, —$R_4OP(OH)_2O^-$, —$R_4OR_5P(OH)_2O^-$, —$R_4OR_5OP(OH)_2O^-$, —$R_4OR_5N(R_6)_3^+$, —$R_4N^+(CH_3)_2CH_2COO^-$, or —$R_4N(CH_3)_3^+R_5SO_3^-$; wherein $R_4$, $R_5$, and $R_6$ are each, independently, lower alkyl, lower alkenyl, lower alkynyl, substituted lower alkyl, substituted lower alkenyl, or substituted lower alkynyl; n is 1 to 6.

12. The surfactant of claim 11, wherein $R_3$ is selected from a group consisting of —$R_4SO_3^-$, —$R_4OR_5SO_3^-$, —$R_4(OCH_2CH_2)_nSO_3^-$.

13. A surfactant represented by the following formula:

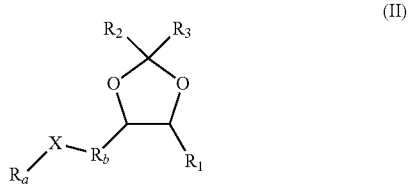

(II)

in which $R_a$ and $R_b$ are each, independently, alkyl, alkenyl, or alkynyl, and $R_a$ is linear or branched $C_5$-$C_{30}$, and $R_b$ is linear or branched $C_1$-$C_5$;

X is $CR'_2$, O, NR', or S; wherein each R' is independently H, lower alkyl, lower alkenyl, or lower alkynyl;

$R_1$ and $R_2$ are each, independently, hydrogen or linear or branched $C_1$-$C_5$; and $R_3$ contains an anionic, a cationic, a zwitterionic, or a non-ionic hydrophilic group.

14. The surfactant of claim 13, wherein $R_3$ is selected from a group consisting of —$R_4SO_3^-$, —$R_4OR_5SO_3^-$, —$R_4(OCH_2CH_2)_nSO_3^-$, —$R_4COO^-$, —$R_4OR_5COO^-$, —$R_4CONCH_3CH_2COO^-$, —$R_4(OCH_2CH_2)_nOP(OH)O_2^-$, —$R_4OP(OH)O_2^-$, —$R_4OP(OH)_2O^-$, —$R_4OR_5P(OH)_2O^-$, —$R_4OR_5OP(OH)_2O^-$, —$R_4N(CH_3)_3^+$, —$R_4N(R_6)_3^+$, —$R_4OR_5N(R_6)_3^+$, —$R_4N^+(CH_3)_2CH_2COO^-$, —$R_4N(CH_3)_3^+R_5SO_3^-$; wherein $R_4$, $R_5$, and $R_6$ are each, independently, lower alkyl, lower alkenyl, lower alkynyl, substituted lower alkyl, substituted lower alkenyl, or substituted lower alkynyl; n is 1 to 6.

15. The surfactant of claim 13, wherein $R_3$ is selected from a group consisting of —$R_4SO_3^-$, —$R_4OR_5SO_3^-$, —$R_4(OCH_2CH_2)_nSO_3^-$.

16. The surfactant of claim 11, wherein the surfactant is selected from the following chemical structures:

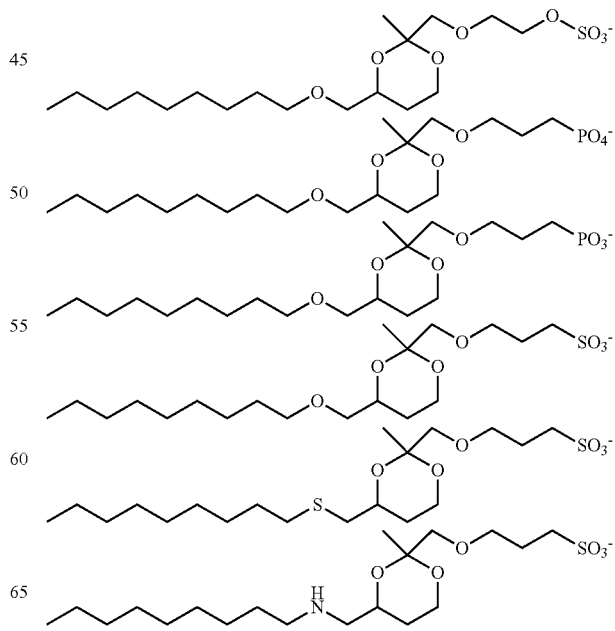

-continued

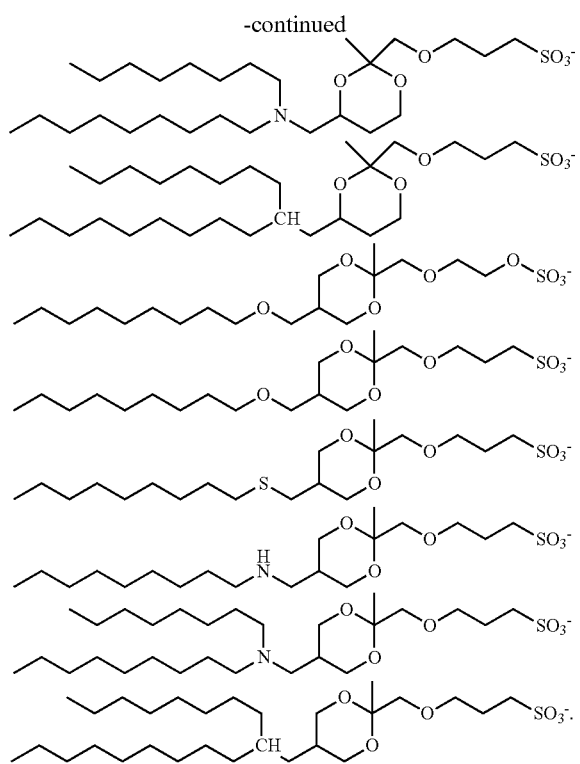

17. The surfactant of claim 11, wherein the surfactant is selected from the following chemical structures:

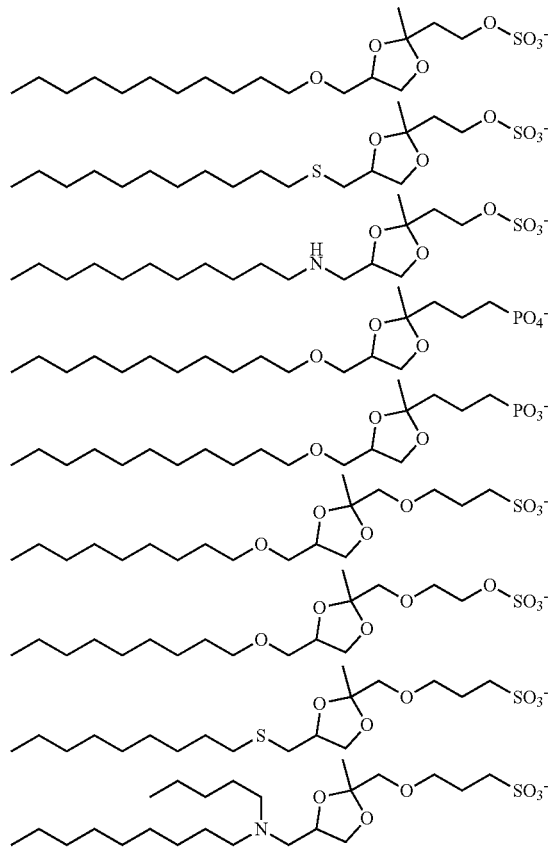

-continued

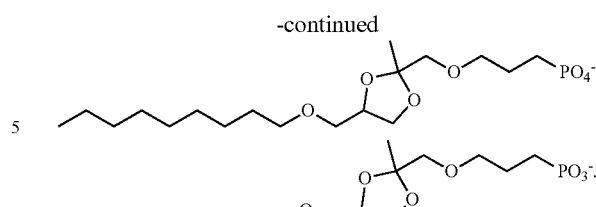

18. A kit for performing protein solubilization or enzyme digestion comprising the surfactant according to claim 11.

19. The kit of claim 18 comprising a solution for degrading the surfactant.

20. A kit for performing protein solubilization or enzyme digestion comprising the surfactant according to claim 13.

21. The kit of claim 18 wherein the surfactant is selected from surfactants having the following chemical structures:

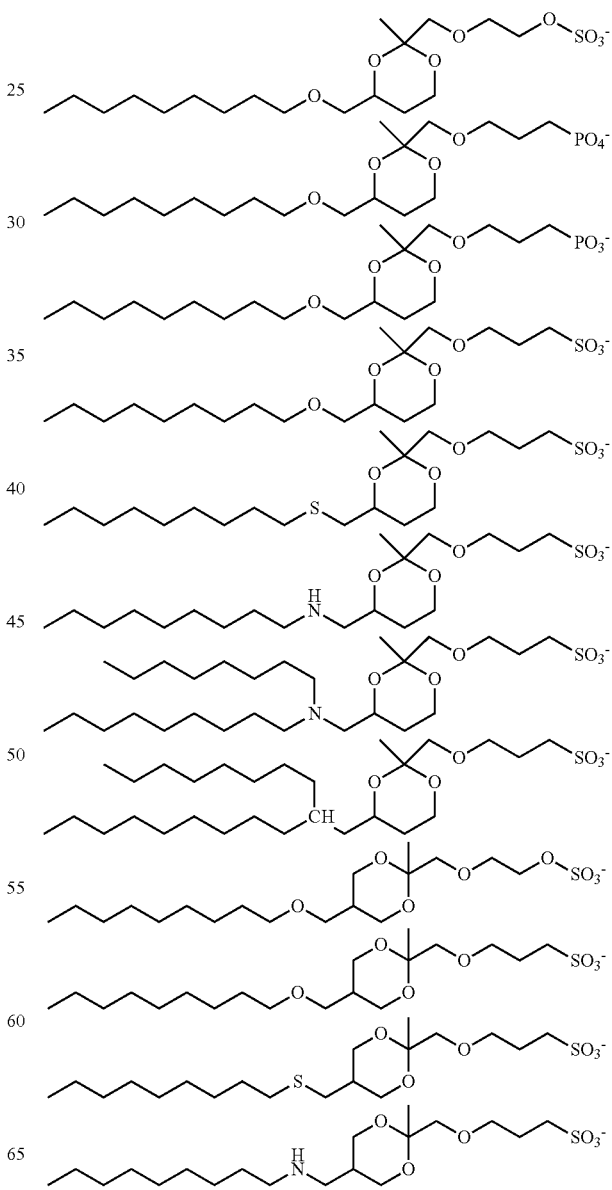

-continued

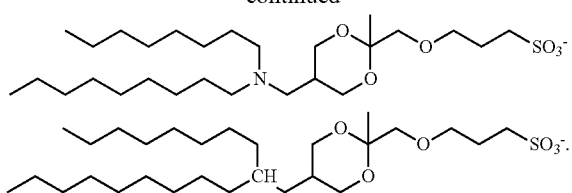

22. The kit of claim 18 wherein the surfactant is selected from surfactants having the following chemical structures:

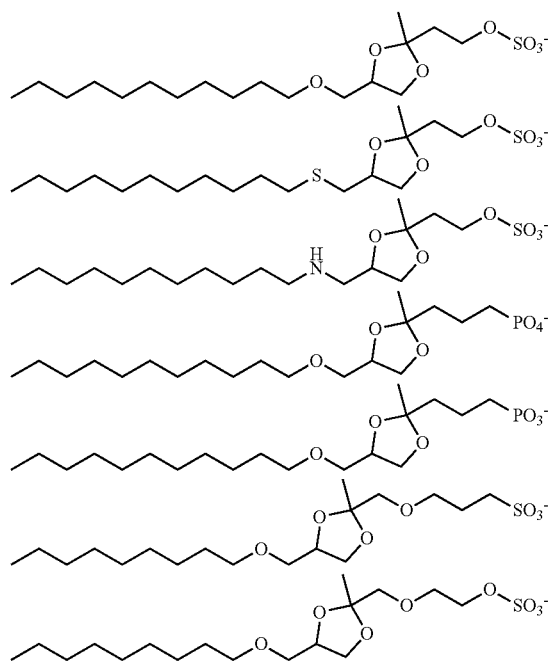

-continued

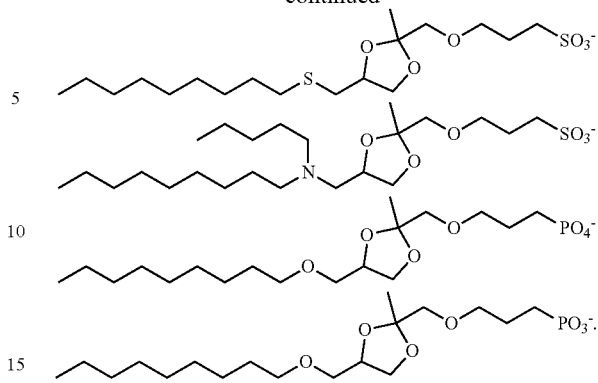

23. A method for analyzing a sample comprising first contacting the sample with the surfactant according to claim 11.

24. The method of claim 23 wherein the step of analyzing the sample comprises high performance liquid chromatography.

25. The method of claim 23 wherein the step of analyzing the sample comprises mass spectrometric detection.

26. The method of claim 23 wherein the step of analyzing the sample comprises ion-pair liquid chromatography.

27. A method of solubilizing a substance comprising contacting a substance with the surfactant according to claim 11.

28. The method of claim 1, wherein $R_3$ is a group selected from —$R_4SO_3^-$, —$R_4OR_5SO_3^-$, —$R_4(OCH_2CH_2)_nSO_3^-$, —$R_4(OCH_2CH_2)_nOP(OH)O_2^-$, —$R_4OP(OH)O_2^-$, —$R_4OP(OH)_2O^-$, —$R_4OR_5P(OH)_2O^-$, —$R_4OR_5OP(OH)_2O^-$, or —$R_4N(CH_3)_3^{3O}R_5SO_3^-$.

29. The method of claim 11, wherein $R_3$ is a group selected from —$R_4SO_3$, —$R_4OR_5SO_3^-$, —$R_4(OCH_2CH_2)_nSO_3^-$, —$R_4(OCH_2CH_2)_nOP(OH)O_2^-$, —$R_4OP(OH)O_2^-$, —$R_4OP(OH)_2O^-$, —$R_4OR_5P(OH)_2O^-$, —$R_4OR_5OP(OH)_2O^-$, or —$R_4N(CH_3)_3^{3O}R_5SO_3^-$.

* * * * *